United States Patent
Polejaeva et al.

(10) Patent No.: US 9,999,206 B2
(45) Date of Patent: Jun. 19, 2018

(54) MODEL AND METHOD FOR A TRANSGENIC BOVIDAE EXPRESSING CARDIAC FIBROSIS AND ASSOCIATED PATHOLOGY

(71) Applicant: Utah State University, North Logan, UT (US)

(72) Inventors: Irina Polejaeva, Logan, UT (US); Zhongde Wang, North Logan, UT (US); Shengwei Hu, Logan, UT (US); Ravi Ranjan, Salt Lake City, UT (US); Aaron James Thomas, Logan, UT (US); Christopher Joseph Davies, Logan, UT (US); Kenneth L. White, North Logan, UT (US)

(73) Assignee: Utah State University, Logan, UT (US)

( * ) Notice: Subject to any disclaimer, the term of this patent is extended or adjusted under 35 U.S.C. 154(b) by 163 days.

(21) Appl. No.: 14/341,692

(22) Filed: Jul. 25, 2014

(65) Prior Publication Data
US 2015/0033370 A1    Jan. 29, 2015

Related U.S. Application Data

(60) Provisional application No. 61/858,430, filed on Jul. 25, 2013.

(51) Int. Cl.
*A01K 67/00* (2006.01)
*A01K 67/027* (2006.01)
*C07K 14/495* (2006.01)

(52) U.S. Cl.
CPC ...... *A01K 67/0275* (2013.01); *A01K 67/0278* (2013.01); *C07K 14/495* (2013.01); *A01K 2217/072* (2013.01); *A01K 2217/206* (2013.01); *A01K 2227/102* (2013.01); *A01K 2267/0375* (2013.01)

(58) Field of Classification Search
CPC ............... A01K 67/0275; A01K 2227/102
See application file for complete search history.

(56) References Cited

U.S. PATENT DOCUMENTS

| | | | |
|---|---|---|---|
| 2004/0073958 A1* | 4/2004 | Katsuki | A01K 67/0275 800/8 |
| 2004/0213794 A1* | 10/2004 | Vatner | A61K 38/45 424/155.1 |

OTHER PUBLICATIONS

Naito et al. J Reprod Fert 113:137-143, 1998.*
Raina et al. Gene 96-100, 2015.*
Schuttumpf et al. Human Gene Therapy 22:101-106, 2011.*
Dolatshad et al. Mamm. Genome 26:598-608, 2015.*
Kong et al. PLosONE 4(8):e6679, 2009, pp. 1-10.*
Nakajima et al., Atrial but not ventricular fibrosis in mice expressing a mutant transforming growth factor-beta(1) transgene in the heart, Circulation Research, 2000, 571-579, vol. 86, Issue 5.
Verheule et al., Increased Vulnerability to Atrial Fibrillation in Transgenic Mice With Selective Atrial Fibrosis Caused by Overexpression of TGF-beta(1), Circulation Research Apr. 29, 2004, 1458-1465, vol. 94, Issue 11.
Zou et al., Oxidase-deficient neutrophils from X-linked chronic granulomatous disease iPS cells: functional correction by zinc finger nuclease-mediated safe harbor targeting, Blood Journal, Mar. 16, 2011, 5561-5572, vol. 117, Issue 21.
Polejaeva et al., Increased Susceptibility to Atrial Fibrillation Secondary to Atrial Fibrosis in Transgenic Goats Expressing Transforming Growthing Factor-B1, 27:10 Journal of Cardiovascular Electrophysiology 1220-1229 (Oct. 2016).

* cited by examiner

Primary Examiner — Marcia S Noble

(57) ABSTRACT

Herein provided are a model and method for a transgenic a bovidae having an TGF-β1 gene inserted into the bovidae genome and capable of expressing higher than normal levels of TGF-β1 in cardiac muscle.

5 Claims, 10 Drawing Sheets

TALENs activity test by surveyor assay

WT: CTCCCTACCAGGGACACGGCAGGGCACCATCCCTC  SEQ ID NO. 35
1#: CTCCCTACCAGGGAC........CAGGGCACCATCCCTC  SEQ ID NO. 36
6#: CTCCCTACCAGGGACA............GGCACCATCCCTC  SEQ ID NO. 37
15#: CTCCCTACCAGGGA......GGCAGGGCACCATCCCTC  SEQ ID NO. 38
22#: CTCCCTACCAGGGAC....GGCAGGGCACCATCCCTC  SEQ ID NO. 39

```
WT:   CGACTGGTGGGGGACACGGCAGGGCGGTGGTCAG   SEQ ID NO. 40
1#:   CGACTGGTGGGGGAC......GCAGGGCGGTGGTCAG  SEQ ID NO. 41
6#:   CGACTGGTGGGGGACA......CAGGGCGGTGGTCAG  SEQ ID NO. 42
15#:  CGACTGGTGGGGGACA....GCAGGGCGGTGGTCAG   SEQ ID NO. 43
22#:  CGACTGGTGGGGGACAC..........GCGGTGGTCAG SEQ ID NO. 44
```

Figure 13

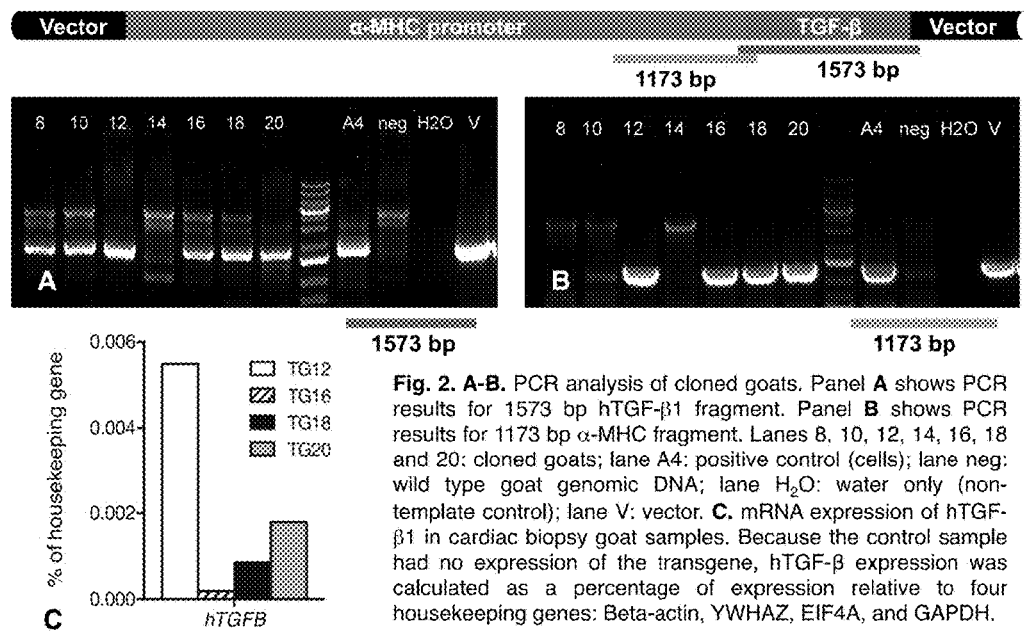

Fig. 2. A-B. PCR analysis of cloned goats. Panel A shows PCR results for 1573 bp hTGF-β1 fragment. Panel B shows PCR results for 1173 bp α-MHC fragment. Lanes 8, 10, 12, 14, 16, 18 and 20: cloned goats; lane A4: positive control (cells); lane neg: wild type goat genomic DNA; lane H₂O: water only (non-template control); lane V: vector. C. mRNA expression of hTGF-β1 in cardiac biopsy goat samples. Because the control sample had no expression of the transgene, hTGF-β expression was calculated as a percentage of expression relative to four housekeeping genes: Beta-actin, YWHAZ, EIF4A, and GAPDH.

Figure 14

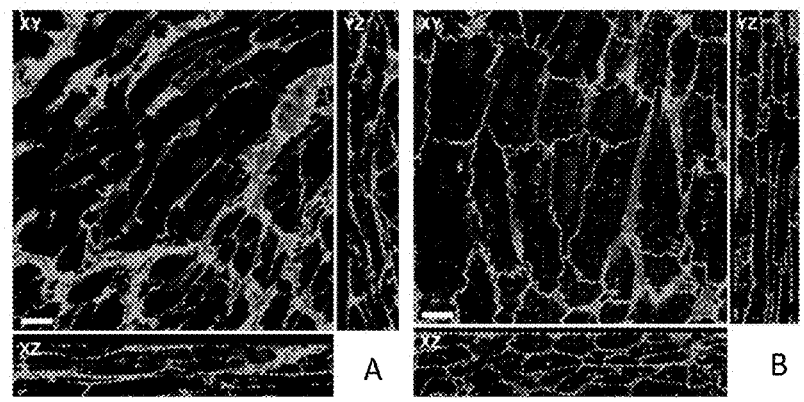

United States Patent

SEQUENCE LISTING

```
<160> NUMBER OF SEQ ID NOS: 44

<210> SEQ ID NO 1
<211> LENGTH: 4897
<212> TYPE: DNA
<213> ORGANISM: Capra aegagrus

<400> SEQUENCE: 1
tttggaagaa gcagaataaa gcaatttcc ttgaagtgag atcctgcctc tagactcttc      60
ttcacagcct gccagccaca ggaacacaag gacatgacca cgggacgggg aggggggctc    120
caggggagga ggccagaccc aggaggcctc cctggggagc ctgggaggct ccgagcatcc    180
ttggtgcggc actgccatgg tctcccgtca cctcctcagc agatgacacc tctcctgtca    240
gccctctccc tggcccagag accctggggg ttaaaggaga tttagagaag cccttgaagc    300
cctcctagag cacgtgagcc catctgtgtt gacctacgcc ccgatctgat caacaccgcc    360
ccccctgctg acaatagcca ggctgggcca tggggaggag gtttaatgtg tgagggtgcc    420
```

```
ctccaaggca tgacccgctt agagtaatga tcccccagtc cccatccgaa gtgagtgtct    480
gagagggcac aggactggca tccgtagctc ctccccttc cagacacagc ttccactgtc      540
tccaactacc ttcccaccat gatcaggaga cctgcactcc agcccacctc ccatctcctc    600
ctgggacctg gcctgtgatc caagacactc tattcttctc cctcattact tcctaccata    660
gcttttggcc ttgctggaag atggaggttc tttggcctgt ttagagcagg tcatctgagg    720
gggaggcaga caaatgaggg gctggggaaa gtcacggtga gcagggccct ggggaaggaa    780
ggggctgggg aggatcacca gagggctgga aagtggagga aggagtaagc tccatctcag    840
ctaaacaagc ccagtcctcc acctgcccca gactcactta gggccatggg gaggaggttt    900
aatgtgtgag ggtgccctcc aaggcatgac ccacttagag taatgatccc tcagtgccac    960
acctgggctg cttagggaat gcctggacca cggagcatgg ggactgagga ggccctggcc   1020
tgcttaggga aggcctggac cacggagcat ggggactgag gaggccctgg cctgaatcct   1080
ccccagtgtg ctacacatgg ccactcccag cccctctggg ctctgagctc caatgcagc    1140 agctaaagtg cctgttccag ggaggagagg aagaggaaag aaggggaaca gggaagggaa   1200
aaggaaagac ctaagcaggt ctgcagtgga gagagaggga gaaggttcaa gaacgtggag   1260
gatggtgaac aaggaaacca acagagagag aatatagagg aagtgaggtg ggtgcccttg   1320
aaagacccac aggctatccc ttcattctct tcacatcctc ctccactctc cctgcctagc   1380
accagtcttc ctaggaaaga ctcggagagg aaatacctgg aggaaagaga gggacacgtg   1440
tgaaaaggaa gatgcggggg atactcagag aatccaagct tccagagcag aaaacagagg   1500
cagagagaac agccagtgcc cacgccgcag acaggccccg aaggaggatg ctgagagggg   1560
atgggagagg agacagagag ggcgagcctt ggatagagaa gctggaagag ccaaggtctg   1620
gtactggcca caggaaagaa tcctgggtca ccctcagatg ccagcaaaat tgagacagcg   1680
gagaacggtt aggttcaaga ggagtggatg aagacccagg agcaggaagt gcaggctgag   1740
atgggacaag cagagggtca gcagaggctg ggctcagaga aaggcagaga cgtgtggaaa   1800
tacaggcatg tcagaccgtg cgatgggcag aaatatggcg ccaggagaa cgggagccca    1860 ggtccagctt tgagaccggg aaccgggcag aggggaaggg agacagacac agagaaggac   1920
agacatacag ggagccaggc aaatgcaggg cttctctcct cggccccta cctgcggcag    1980 gagtgaccaa ccggcacgct caccctccaa gactcctggc agagtaagga gctgcttcgg   2040
gaggacagag agtagggatg gatgtgagag ggagactagg ataggagag gatggcaaac    2100 cagaccagac gggtggggca gaaccctgga accgtgttaa gccctcccct cttcccctt     2160 ccataggaga cagtgggaac cgcctgccta cccctcacca cccctcgact ccatctatac   2220
ccagtctggc ttgctcagaa cataaggttc ctgaggaca aagcctagcc tttgtcacct     2280
ggttctgacc cagtctgacc tgatgttccc agcccttat cacgtcccca gggcaatggg    2340
aactaggcag tgacgcactg gccgcagac taaaccccca gcttgcgtac taggtcctca    2400
agtgacctgg agatggggac aagtagcttt catcccaggg ggaaatgagt tggcatatgt   2460
gcctgcagga gatgggaatg tgggttgact acggtccccc caaggacatg ggtatagggt   2520
acaagtcccc tggagacaga tgtgtaatcc tgagtcccac agtggggcag tggagggccc   2580
tagggagttg agaccatgc aggagagacc acataattgg tggaaagcag agaagccgac    2640
ccccatccgt cctacccacc tccacactct agagctatat tgagaggtga caggagatgg   2700
tttgggaggg ggagcctggg agcatgttcc tgggtgtgag ggtgtaggga aagccagggc   2760
```

| | | | | | |
|---|---|---|---|---|---|
| agcagagtct | ggctttgttt | cctgaacaca | atgtccactt | agtcataaca | ggcatggcta | 2820 |
| ctgcctctga | gaggtggcat | cactggaggc | agggagggg | gccacaaggg | cctgaggcgc | 2880 |
| ttggggacac | tctccaagaa | ggacatgtga | gtatgagccc | catgagggtt | gagaggcgac | 2940 |
| accaggttc | tacctgggga | gacgggagcg | gactgcagag | cccccaccct | gtggaatgcc | 3000 |
| aagcttgggg | cccagctggt | gtaaatcccg | gggattgcca | gggccccagt | cagcctcagc | 3060 |
| agcacctgca | ccctctggca | gcccaggag | gcggaaggga | gcaccccac | cctcaccct | 3120 |
| cctgcctcag | gccccgggga | ttaacgcctc | tcccaccccc | atcccatccc | acaatgggag | 3180 |
| cagaggatgg | cagtgaaggg | taaaagcttc | tgtgtgcaaa | tgtgcgtttg | ggtgtgcaaa | 3240 |
| acaacgcaga | ggaaaatctg | caaactgaag | tatgtaagag | tggaaaaccc | tcatgtgtgt | 3300 |
| gttaagactg | ggcatggacc | cgtggtggcc | aagtctggac | agtagatggc | tggactgcgg | 3360 |
| gtctgtgtgc | acctctgcca | tggtggcatg | ggggaactcc | gtcttctgct | tgacaggtca | 3420 |
| gacagtggcc | actgtatcag | gagcgtcggg | gaggggctgg | gggctccgga | tgtgtcccta | 3480 |
| atgtaatgca | acctcacgtt | cccaggagga | cacctgcctg | cagacagggg | aaaacacaga | 3540 |
| aagagagggc | agcacgaaat | tcttttcctg | acaaagggaa | actgagtcaa | ggacccgggt | 3600 |
| agtggcgccc | ctccctgggc | gtcctggctc | agcagccag | gccccagcac | catagggctc | 3660 |
| caggaccaga | gagggtgggg | agctgctccc | agcctgggc | cgtgtgagga | caggccaggg | 3720 |
| aggaaaggag | gaggggagcc | cgtggctggg | aggcagggga | caagcctctg | gtctgcagga | 3780 |
| gaaggtggcc | ctcaccccgt | gtgctcaact | cacccttcag | attaaaaata | accaaggtaa | 3840 |
| gggcttgatg | ggggggtggc | aggggggagg | tggtatgaga | agtcctgtct | tgccactatc | 3900 |
| ggcccatcag | tcttttggag | gggaggaatg | tgcccaagga | ctaaaaaaag | gccctggagc | 3960 |
| cagagggggct | ggggcgacag | acctttcatg | ggcaaatctg | gagtcccggt | gtcctcttgt | 4020 |
| cacctccaga | gccaagggat | caagggagga | ggggctggga | ggagagagag | gtggaaggga | 4080 |
| gggtccctcc | ggaaggactc | caaatttagg | caggggtgg | gggcagcgaa | atataaagga | 4140 |
| gtgtgctcca | aggacagact | gacactcctc | tgagccaggt | aaggtggggc | tcagggtggg | 4200 |
| agcccccatc | tcgaaaggga | atggggtgag | atcagtcgga | ggcccaagg | gtttctgctt | 4260 |
| gaactgtctt | gctccagccc | tgggaagttg | ccccgacag | aggggaggt | tcccagggga | 4320 |
| aaaccagaaa | cctctttct | tctcctaccg | gcatgtcctc | cccggctttc | gtctcttcca | 4380 |
| tgtgctttct | tccccttgt | ccctccttgg | atggcttccc | tcttgcaatc | cagttttttt | 4440 |
| tttttttt | tttaagggag | gatagttata | atattgtgat | ggttcttgcc | atacatcaac | 4500 |
| atgaattggc | cacgggtggt | tcagttttat | ttttcctctt | ggttttgtc | agcacttgtc | 4560 |
| actatcatac | ttcctggtct | gtctctcttc | ctgcccctct | tggctgtgtg | ctctaatctc | 4620 |
| cttgcatctc | tctgtttcaa | acgcagattc | cacaccctac | tccttgcact | ttgactaact | 4680 |
| ctgcatcctc | tcttccctgt | ctctccgcct | ctcaccgcc | cctgactgcc | ctttcagtc | 4740 |
| tgtcccgctc | aggtgactcc | ctggcttgag | actcacagct | tgcttctccc | cgtgggctgc | 4800 |
| cccttgttc | ttcattctcc | ttgtctcttc | tctctgctca | gctgcacctc | tgtggctcac | 4860 |
| ggtccagggt | cttcaggatt | ctctgtgaag | aggtcac | | | 4897 |

<210> SEQ ID NO 2
<211> LENGTH: 521
<212> TYPE: DNA
<213> ORGANISM: Capra aegagrus

<400> SEQUENCE: 2

```
gccccgcccc cctcccaggt tcgcaggggc ctggcaatcc cgcatggcct tgggccccag      60
ggtccggctg tctccctacc agggacacgg cagggcggtg gtcagctctc ctggagagtc     120
tgctgggtct gaggaggagg gcctgggtct cttcccttgg gttcagctct ggggccccat     180
cctccatggt gactggggtg cgtctcctga acaagcatag ttcggatccc ctacagctcc     240
tctcctctct ggccagcttc tcctctcacg gtccccagtg agcccagag gcctgcctgg      300 cgtggccacc gggaagccag gctgtgcagg gctgggggtg ccctgcggac atggtgcctt     360
ccagggacct tggggtcttc ctctggagcc ttgctcggtc ggccctgggt cccctcgag      420 gccctgcctt gcaaggcacg tggaggggtc cggggtggtg aggtgacccc ccgccgtgc     480 ccccaggcc tgcattgacg agaaccttga ggtggtgcgc t                          521
```

<210> SEQ ID NO 3
<211> LENGTH: 53
<212> TYPE: DNA
<213> ORGANISM: Artificial Sequence
<220> FEATURE:
<223> OTHER INFORMATION: Primer

<400> SEQUENCE: 3

```
tccggctgtc tccctaccag ggacacggca gggcggtggt cagctctcct gga            53
```

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4

```
gagttgtgcg gcagtggttg a                                               21
```

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5

```
gtagtgaacc cgttgatgtc ca                                              22
```

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6

```
tctcttgtgc tacccagctc ta                                              22
```

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7

```
gaggtcactt gaggctcctg t                                               21
```

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
gtatgagcac cagaacagca ga                                              22

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
gaagttctca gtggcaggag gtt                                             23

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
ccacaccaga aatgacagac aga                                             23

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gatgcgcttc cgcttcacca                                                 20

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
agtggcacct tccagggtca a                                               21

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
agacaggatg aggatcgttt cgca                                            24

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
gcggtggaat cgaaatctcg tgat                                              24

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
tggtgctgac ggacctgct                                                    19

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cacaccacgc tgtccagcaa                                                   20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ctggtgagcc tggtgaacct                                                   20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
catcctcacc agccttgcca                                                   20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
cacgcaaggc cgtcagacta                                                   20

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
agggccaatg tccgcacca                                                    19

<210> SEQ ID NO 21

-continued

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
cacacccttg actcctgttg t                                        21

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
ctcttcactc agctcatact cca                                      23

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
gagttgtgcg gcagtggttg a                                        21

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
gtagtgaacc cgttgatgtc ca                                       22

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
cagcagatct tcgacgtcag gtggcactt                                29

<210> SEQ ID NO 26
<211> LENGTH: 34
<212> TYPE: DNA
<213> ORGANISM: Artificial Sequence
<220> FEATURE:
<223> OTHER INFORMATION: Primer

<400> SEQUENCE: 26
gtcgaagatc tgctgcccct ttggaagaag caga                          34

<210> SEQ ID NO 27
<211> LENGTH: 36
<212> TYPE: DNA
<213> ORGANISM: Artificial Sequence
<220> FEATURE:
<223> OTHER INFORMATION: Primer

<400> SEQUENCE: 27
ggtggctcga ggtgacctct tcacagagaa tcctga                                36

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
tcacctcgag ccaccacacc agccctgtt                                        29

<210> SEQ ID NO 29
<211> LENGTH: 29
<212> TYPE: DNA
<213> ORGANISM: Artificial Sequence
<220> FEATURE:
<223> OTHER INFORMATION: Primer

<400> SEQUENCE: 29
tgggaattcg cgggacctca gctgcactt                                        29

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
tcccgcgaat tcccaccata ttgccgtctt                                       30

<210> SEQ ID NO 31
<211> LENGTH: 33
<212> TYPE: DNA
<213> ORGANISM: Artificial Sequence
<220> FEATURE:
<223> OTHER INFORMATION: Primer

<400> SEQUENCE: 31
gaccgatcga tccaaagccc aggcaaacac gtt                                   33

<210> SEQ ID NO 32
<211> LENGTH: 32
<212> TYPE: DNA
<213> ORGANISM: Artificial Sequence
<220> FEATURE:
<223> OTHER INFORMATION: Primer

<400> SEQUENCE: 32
ttggatcgat cggtcatcat caccatcacc at                                    32

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
gctgcccctt tggaagaagc aga                                              23

<210> SEQ ID NO 34
<211> LENGTH: 25
<212> TYPE: DNA

```
<213> ORGANISM: Artificial Sequence
<220> FEATURE:
<223> OTHER INFORMATION: Primer

<400> SEQUENCE: 34
gtgacctctt cacagagaat cctga                                              25

<210> SEQ ID NO 35
<211> LENGTH: 35
<212> TYPE: DNA
<213> ORGANISM: Artificial Sequence
<220> FEATURE:
<223> OTHER INFORMATION: Primer

<400> SEQUENCE: 35
ctccctacca gggacacggc agggcaccat ccctc                                   35

<210> SEQ ID NO 36
<211> LENGTH: 31
<212> TYPE: DNA
<213> ORGANISM: Artificial Sequence
<220> FEATURE:
<223> OTHER INFORMATION: Primer

<400> SEQUENCE: 36
ctccctacca gggaccaggg caccatccct c                                       31

<210> SEQ ID NO 37
<211> LENGTH: 29
<212> TYPE: DNA
<213> ORGANISM: Artificial Sequence
<220> FEATURE:
<223> OTHER INFORMATION: Primer

<400> SEQUENCE: 37
ctccctacca gggacaggca ccatccctc                                          29

<210> SEQ ID NO 38
<211> LENGTH: 32
<212> TYPE: DNA
<213> ORGANISM: Artificial Sequence
<220> FEATURE:
<223> OTHER INFORMATION: Primer

<400> SEQUENCE: 38
ctccctacca gggaggcagg gcaccatccc tc                                      32

<210> SEQ ID NO 39
<211> LENGTH: 33
<212> TYPE: DNA
<213> ORGANISM: Artificial Sequence
<220> FEATURE:
<223> OTHER INFORMATION: Primer

<400> SEQUENCE: 39
ctccctacca gggacggcag ggcaccatcc ctc                                     33

<210> SEQ ID NO 40
<211> LENGTH: 34
<212> TYPE: DNA
<213> ORGANISM: Artificial Sequence
<220> FEATURE:
<223> OTHER INFORMATION: Primer

<400> SEQUENCE: 40
cgactggtgg gggacacggc agggcggtgg tcag                                    34
```

```
<210> SEQ ID NO 41
<211> LENGTH: 31
<212> TYPE: DNA
<213> ORGANISM: Artificial Sequence
<220> FEATURE:
<223> OTHER INFORMATION: Primer

<400> SEQUENCE: 41
cgactggtgg gggacgcagg gcggtggtca g                              31

<210> SEQ ID NO 42
<211> LENGTH: 31
<212> TYPE: DNA
<213> ORGANISM: Artificial Sequence
<220> FEATURE:
<223> OTHER INFORMATION: Primer

<400> SEQUENCE: 42
cgactggtgg gggacacagg gcggtggtca g                              31

<210> SEQ ID NO 43
<211> LENGTH: 32
<212> TYPE: DNA
<213> ORGANISM: Artificial Sequence
<220> FEATURE:
<223> OTHER INFORMATION: Primer

<400> SEQUENCE: 43
cgactggtgg gggacagcag ggcggtggtc ag                             32

<210> SEQ ID NO 44
<211> LENGTH: 28
<212> TYPE: DNA
<213> ORGANISM: Artificial Sequence
<220> FEATURE:
<223> OTHER INFORMATION: Primer

<400> SEQUENCE: 44
cgactggtgg gggacacgcg gtggtcag                                  28
```

US 9,999,206 B2

MODEL AND METHOD FOR A TRANSGENIC BOVIDAE EXPRESSING CARDIAC FIBROSIS AND ASSOCIATED PATHOLOGY

CROSS-REFERENCES TO RELATED APPLICATIONS

This claims priority to U.S. Provisional Patent Application No. 61/858,430 entitled "MODEL AND METHOD FOR A TRANSGENIC GOAT EXPRESSING CARDIAC FIBROSIS AND ASSOCIATED PATHOLOGY" and filed on Jul. 25, 2013 for Irina Polejaeva which is incorporated herein by reference.

BACKGROUND

Field of the Invention

The disclosure provided herein relates to a genetically modified bovidae, specifically a goat, as a model for studying cardiac fibrosis and fibrosis associated cardiac pathologies in human-sized hearts. The disclosure provided further relates to methods by which genetically modified goats and other bovidae may be produced.

Description of the Related Art

Human and animal studies indicate that fibrosis plays a central role in the cardiac remodeling observed in various cardiac diseases. In fibrosis, profibrotic factors act on cardiac cells to increase the deposition of extracellular matrix (ECM). These changes alter the structure, architecture and shape of the heart to affect three aspects of cardiac function: electrical conduction, ventricular contractility and valvular function. Transforming growth factor β1 (TGF-β1) is involved in pathologies associated with each of these cardiac functions.

Small animal models, such as mouse, have been useful for cardiovascular research. However, due to the small heart size, functional electrophysiology of transgenic mice is problematic. Mouse models are also not suitable for advancing the development of implantable devices, ablation therapies, or improved imaging techniques. Mice that overexpress TGF-β1 have profound atrial fibrosis and increased susceptibility to induction of atrial fibrillation via rapid atrial pacing. Atrial fibrosis alters atrial excitability as well as electrical conduction.

Histological analysis of atrial biopsy samples from patients with lone atrial fibrillation (AF) (not caused by an underlying heart disease) showed that 75% of these individuals exhibited atrial fibrosis. Additionally, studies using several animal models found that chronic atrial fibrosis increases AF vulnerability. Furthermore, myocardial fibrosis reduces ventricular compliance, with a two to three-fold rise in collagen volume causing significant ventricular stiffening. Systolic dysfunction is also associated with increased myocardial collagen concentration. TGF-β1 expression is elevated in patients with dilated and hypertrophic cardiomyopathies as well as aortic stenosis and regurgitation. These findings indicate a pivotal role of TGF-β1 in a wide range of cardiac pathologies.

SUMMARY

The Applicants herein have determined that a need exists for a model and method for expressing cardiac fibrosis in an animal heart exhibiting sufficient similarity to the human heart to provide a research tool. Beneficially, such a model and method would increase the level of expression of TGF-β1 while allowing the animal to survive.

The model and method disclosed herein have been developed to provide a transgenic bovidae, for example a goat, expressing heightened TGF-β1 levels and associated cardiac fibrosis that overcomes many or all of the above-discussed shortcomings in the current art.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

Herein provided is a model for a transgenic mammal of the family bovidae expressing cardiac fibrosis. In some embodiments the model comprises a transgenic bovidae having a Human Transforming Growth Factor β1 (hTGF-β1) gene inserted at least one of randomly and into an appropriate locus of the bovidae genome, wherein the bovidae is capable of expressing higher than normal levels of TGF-β1 in cardiac muscle. In various embodiments the bovidae exhibits at least one of atrial fibrosis, elevated levels of extracellular matrix (ECM) gene expression, increased ECM volume, elevated ventricular fibroblast fraction, and increased susceptibility to AF induction.

In certain embodiments the bovidae is a goat. The locus sometimes comprises at least one of AAVS1, CCR5, and aMHC. The hTGF-β1 gene may comprise a pcDNA3.1DV5-MHC-TGF-β1 vector and the pcDNA3.1DV5-MHC-TGF-β1 vector sometimes comprises a cysteine to serine substitution at residue 33. In some embodiments the goat α-MHC promoter comprises SEQ ID NO. 1. The goat AAV1 gene may comprise SEQ ID NO. 2.

In various embodiments the atrial fibrosis may develop progressively. Thus, this novel TGF-β1 model may allow for monitoring the gradual progression of atrial fibrosis and related pathologies in a heart similar in size and physiology to the human heart and in a way that parallels human disease development. The bovidae is sometimes apparently healthy at birth. In some embodiments the bovidae is a sheep.

Further provided herein is a method for at least one of a bovidae embryo, blastocyst, fetus and animal expressing cardiac fibrosis TGF-β1. In some embodiments the method comprises: producing a cytoplast by removal (enucleation) of genetic material (DNA/metaphase II plate) from an oocyte using either micromanipulation pipette or by cutting an oocyte into at least two parts obtaining at least one cytoplast; inserting a transfected fibroblast donor cell nucleus comprising a TGF-β1 under control of α-MHC promoter inserted AAVS1 locus into the cytoplast; fusing at least one karyoplast (donor cell or nucleus) with one cytoplast resulting in a reconstructed embryo; activating the reconstructed embryo to induce embryonic development; and transferring the reconstructed embryo into a surrogate recipient goat at least one of immediately after activation or after in vitro embryo culture such that the embryo develops into a genetically modified fetus.

In various embodiments of method provided the bovidae is a goat. The TGF-β1 may be human TGF-β1. The method sometimes comprises constructing a pcDNA3.1DV5-MHC-TGF-β1 vector by subcloning the MHC-TGF-β1 fragment from the plasmid pUC-BM20-MHC-TGF-β1 into the pcDNA3.1D V5 vector. In some embodiments the method comprises effecting a cysteine-to-serine substitution at amino acid residue 33 of the pcDNA3.1DV5-MHC-TGF-β1 vector. The method sometimes comprises cloning and characterizing an ~9 kb goat genomic fragment covering the polyadenylation site of the goat α-MHC gene, wherein the sequence comprises an ~7 kb fragment of the goat intergenic region between the α-MHC and IL25 genes and a ~2 kb fragment of goat genomic DNA immediately upstream of the goat α-MHC polyA site. In certain embodiments the method further comprises building an IRES-hTGF-β1 construct by subcloning the coding sequence of TGF-β1 into the MCS B locus of the vector pIRES and subcloning the 5' and 3' homologous arms into the MCS A and MCS B sites of the IRES-hTGF-β1 vector using the appropriate restriction sites. The method disclosed herein sometimes uses Transcription Activator-Like Effector Nuclease (TALEN) to facilitate insertion of the vector into the AAVS1 locus. According to the method provided the bovidae is sometimes a sheep.

These features and advantages of the present invention will become more fully apparent from the following description and appended claims, or may be learned by the practice of the invention as set forth hereinafter.

BRIEF DESCRIPTION OF THE DRAWINGS

The drawings below are supplied in order to facilitate understanding of the Description and Examples provided herein.

FIG. 13 depicts mRNA expression of hTGF-β in cardiac biopsies of transgenic goats according to the present invention. Because the control samples had no expression of the transgene, hTGF-β1 expression was calculated as a percentage of housekeeping gene expression; and FIG. 14 depicts cross sections of 3-D confocal image stacks from RV biopsies obtained from: A—a 12-month old TGF-β1 transgenic goat according to the present invention and B—an age, weight and sex matched control goat. Fibrous tissues labeled with wheat germ agglutinin (WGA), DAPI, and anti-vimentin show as black and gray scale. Scale bars: A-B—20 stack size: 204.8×204.8×40 μm.

DETAILED DESCRIPTION

Figure 1:
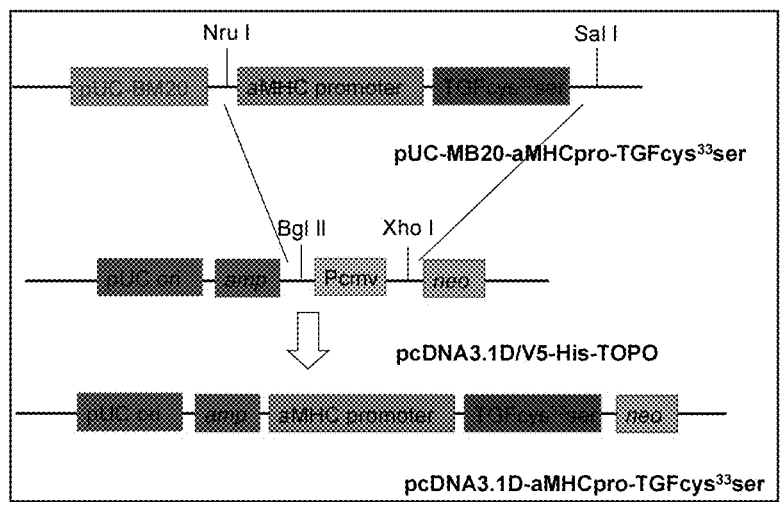
FIG. 1 depicts an embodiment pcDNA3.1DV5-MHC-TGF-β1cys33ser vector construction according to the present invention.

Reference throughout this specification to "one embodiment," "an embodiment," or similar language means that a particular feature, structure, or characteristic described in connection with the embodiment is included in at least one embodiment of the transgenic goat model provided herein. Thus, appearances of the phrases "in one embodiment," "in an embodiment," and similar language throughout this specification may, but do not necessarily, all refer to the same embodiment.

Furthermore, the described features, structures, or characteristics of the transgenic goat model may be combined in any suitable manner in one or more embodiments. In the following description, numerous specific details are provided, to provide a thorough understanding of embodiments. One skilled in the relevant art will recognize, however, that the transgenic goat model may be practiced without one or more of the specific details, or with other methods, components, materials, and so forth. In other instances, well-known structures, materials, or operations are not shown or described in detail to avoid obscuring aspects of the transgenic goat model.

The depicted order and the labeled steps depicted in schematic diagrams are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Introduction

The transgenic goat model with cardiac-specific overexpression of TGF-β1 provided herein may improve current knowledge of the relationship between TGF-β1 and cardiac fibrosis in vivo in human-size hearts and also may generate new knowledge of the role of fibrosis in susceptibility to AF initiation. The essential role of fibrosis in heart disease may give this transgenic model broad application in studies of fibrosis in ventricular contractility and valve function pathologies.

For non-limiting example, the disclosed transgenic goat model with cardiac-specific overexpression of TGF-β1 may provide a platform for clinical and academic researchers investigating the effect of fibrosis on pathological changes in ventricular contractility, valve function and electrical conduction. The model may be relevant to clinical practice because of its potential to open new targets for the prevention and treatment of fibrosis and AF using both pharmacological and non-pharmacological approaches. The transgenic goat model provided herein may complement other existing surgical models (e.g., an AF model using rapid atrial pacing and a heart failure (HF) model using microsphere injections to mimic thromboembolic heart failure) to expand understanding of fibrosis in heart diseases.

The disclosed transgenic goat model with cardiac-specific overexpression of TGF-β1 may provide a useful model for studies of the role of TGF-β1 in fibrosis initiation and progression in human-sized hearts. The model will advance understanding of fibrotic events that occur downstream from TGF-β1 and help to develop and test anti-fibrotic therapies. The TGF-β1 transgenic goats may also be valuable for analyses of wavelet reentry and progressive atrial fibrotic changes. Atrial fibrosis is common in AF. Some aspects of AF-related remodeling have been studied in a non-transgenic goat model. Moreover, some of the key principles of AF, such as 'AF begets AF', originated from goat model studies. However, these AF models are mechanically induced (e.g., the rapid atrial pacing model), which is not the way AF develops in humans. Therefore, existing goat models cannot answer whether atrial fibrosis is an important step on the way to AF in human-sized hearts. In contrast, the cardiac fibrosis in model herein provided is induced by a cardiac specific overexpression of an active form of TGF-β1. Thus this transgenic caprine model may provide a genetic foundation to answer this question and to open new clinically relevant targets for the prevention and treatment of fibrosis and AF. Additionally, the disclosed transgenic goat model may allow researchers to harness the power of genetic engineering coupled with existing surgical models to expand understanding of the role played by TGF-β1 in heart disease and healing.

Furthermore, the transgenic goat model provided herein may facilitate development of noninvasive monitoring of myocardial fibrosis via imaging and serological markers, and advance both pharmacological and non-pharmacological approaches to treat fibrosis associated cardiac conditions. The model may also expedite the development of novel therapeutic applications, devices and diagnostic tools for fibrosis and fibrosis-related cardiac pathologies.

TGF-β1 in the Development of Fibrosis

The mechanisms that underlie cardiac fibrosis have begun only recently to emerge. Several interrelated physiological pathways appear to regulate interstitial fibrosis: the rennin-angiotensin-aldosterone system (RAAS); inflammation, oxidative stress pathways; and TGF-β1 signaling. TGF-β1 has a potent profibrotic function and is central to the signaling cascades implicated in fibrosis. TGF-β1 and its family members are among the few cytokines known to stimulate collagen synthesis. Cardiac fibroblasts play an active role in fibrosis, and TGF-β1 stimulates these cells to synthesize and secrete many ECM proteins, including type I collagen, fibronectin and proteoglycans. TGF-β1 also inhibits the expression of proteases such as collagenase, enhances the expression of protease inhibitors, acts as a paracrine signal to increase myocyte hypertrophy, and functions as an autocrine signal to stimulate cardiac fibroblast proliferation. TGF-β1 is stored in the ECM and can be released by matrix metalloproteinases. TGF-β1 is generated primarily by fibroblasts and acts via the SMAD signaling pathway to stimulate fibroblast proliferation and differentiation into myofibroblasts. Post-transcriptional regulation of TGF-β1 is complex. TGF-β1 is secreted as a large latent multi-protein complex that is subsequently bound to the ECM. Secreted TGF-β1 is bound to the latency-associated peptide (LAP) as an inactive homodimer. Much of the TGF-β1-LAP complex is present in the ECM because LAP is covalently bound to an ECM-anchored protein, the latent TGF-β1-binding protein 1 (LTBP-1). TGF-β1 becomes active as a receptor ligand once it is released from this complex.

Creating a Transgenic Goat Model of Cardiac Fibrosis

Several strategies using site-directed mutagenesis of the LAP have been developed to increase the amount of active TGF-β1. Nakajima et al. created a cysteine-to-serine substitution at amino acid residue 33 (cys33ser) of the human TGF-β1 protein to prevent its covalent binding to the small latent complex and LTBP-1 [1]. In mice, TGF-β1 overexpression was restricted to cardiac tissue by linking the human TGF-β1 cys33ser coding sequence to the α-MHC cardiac specific promoter. α-MHC is a highly expressed cardiac muscle specific protein, and the α-MHC promoter is used to achieve cardiac specific transgene expression. A transgenic MHC-TGF-β1 cys33ser mouse model has been developed and shown to have profound atrial fibrosis and inducible atrial fibrillation [1,2]. The level of active TGF-β1 in the heart of one transgenic line was 30-fold higher than controls. Interestingly, despite equally high expression of TGF-β1 in the atrium and ventricles, only atrial interstitial fibrosis was observed. One explanation may be the known differences in the contribution of cardiomyocytes to the atria and ventricles; cardiomyocytes account for approximately 45% of atrial myocardium volume and 76% in the ventricular volume. Because the number of cardiomyocytes and ECM-secreting fibroblasts are inversely related, atria have a much higher number of fibroblasts that produce extracellular matrix proteins. These studies pioneered in mice show that TGF-β1 overexpression in the heart may provide other models for cardiac fibrosis. Pig models have typically been used for large animal and cardiac models because of their structural and immunological similarity to humans. However, while overexpression of TGF-β1 in pig cardiac myocytes leads to fibrosis, and the concomitant susceptibility to AF, the pigs typically die of heart failure even before being subjected to experimentation. Although the same problem could have been expected in goats, the methods and procedures provided herein resulted in transgenic goats that could withstand overexpression of TGF-β1 in cardiac myocytes. Furthermore, in contrast to mechanical models, in which AF is induced rapidly, the transgenic approach herein disclosed allows for monitoring the gradual progression of atrial fibrosis and AF in a heart similar in size and physiology to the human heart and in a way that parallels human disease development.

EXAMPLES

Example 1. Vector Construction

Mouse α MHC Promoter

A pcDNA3.1DV5-MHC-TGF-β1cys33ser vector was constructed by subcloning the MHC-TGF-β1 fragment from the plasmid pUC-BM20-MHC-TGF-β1 (Nakajima et al., 2000[1]) into the pcDNA3.1D V5 vector (FIG. 1). A cysteine-to-serine substitution at amino acid residue 33 prevented covalent binding between the small latent complex and LTBP-1. This greatly increased the amount of active TGF-β1. The Neon™ transfection system was used to electroporate primary goat fetal fibroblasts. After two weeks of G418 selection, the resulting G418 resistant colonies were screened by PCR to confirm transgene integration into goat genomic DNA. PCR positive cells were used for SCNT.

The Goat α-MHC promoter sequence is as follows (SEQ ID NO. 1):

```
TTTGGAAGAAGCAGAATAAAGCAATTTTCCTTGAAGTGAGATCCTGCCTC
TAGACTCTTCTTCACAGCCTGCCAGCCACAGGAACACAAGGACATGACCA
CGGGACGGGGAGGGGGCTCCAGGGGAGGAGGCCAGACCCAGGAGGCCTC
CCTGGGGAGCCTGGGAGGCTCCGAGCATCCTTGGTGCGGCACTGCCATGG
TCTCCCGTCACCTCCTCAGCAGATGACACCTCTCCTGTCAGCCCTCTCCC
TGGCCCAGAGACCCTGGGGGTTAAAGGAGATTTAGAGAAGCCCTTGAAGC
CCTCCTAGAGCACGTGAGCCCATCTGTGTTGACCTACGCCCCGATCTGAT
CAACACCGCCCCCCCTGCTGACAATAGCCAGGCTGGGCCATGGGGAGGAG
GTTTAATGTGTGAGGGTGCCCTCCAAGGCATGACCCGCTTAGAGTAATGA
TCCCCCAGTCCCCATCCGAAGTGAGTGTCTGAGAGGGCACAGGACTGGCA
TCCGTAGCTCCTCCCCCTTCCAGACACAGCTTCCACTGTCTCCAACTACC
TTCCCACCATGATCAGGAGACCTGCACTCCAGCCCACCTCCCATCTCCTC
CTGGGACCTGGCCTGTGATCCAAGACACTCTATTCTTCTCCCTCATTACT
TCCTACCATAGCTTTTGGCCTTGCTGGAAGATGGAGGTTCTTTGGCCTGT
TTAGAGCAGGTCATCTGAGGGGGAGGCAGACAAATGAGGGGCTGGGGAAA
GTCACGGTGAGCAGGGCCCTGGGGAAGGAAGGGGCTGGGGAGGATCACCA
GAGGGCTGGAAAGTGGAGGAAGGAGTAAGCTCCATCTCAGCTAAACAAGC
CCAGTCCTCCACCTGCCCCAGACTCACTTAGGGCCATGGGGAGGAGGTTT
AATGTGTGAGGGTGCCCTCCAAGGCATGACCCACTTAGAGTAATGATCCC
TCAGTGCCACACCTGGGCTGCTTAGGGAATGCCTGGACCACGGAGCATGG
GGACTGAGGAGGCCCTGGCCTGCTTAGGGAAGGCCTGGACCACGGAGCAT
GGGGACTGAGGAGGCCCTGGCCTGAATCCTCCCCAGTGTGCTACACATGG
CCACTCCCAGCCCCTCTGGGCTCTGAGCTCCCAATGCAGCAGCTAAAGTG
CCTGTTCCAGGGAGGAGAGGAAGAGGAAAGAAGGGGAACAGGGAAGGGAA
AAGGAAAGACCTAAGCAGGTCTGCAGTGGAGAGAGAGGGAGAAGGTTCAA
GAACGTGGAGGATGGTGAACAAGGAAACCAACAGAGAGAGAATATAGAGG
AAGTGAGGTGGGTGCCCTTGAAAGACCCACAGGCTATCCCTTCATTCTCT
TCACATCCTCCTCCACTCTCCCTGCCTAGCACCAGTCTTCCTAGGAAAGA
CTCGGAGAGGAAATACCTGGAGGAAAGAGAGGGACACGTGTGAAAAGGAA
GATGCGGGGATACTCAGAGAATCCAAGCTTCCAGAGCAGAAAACAGAGG
CAGAGAGAACAGCCAGTGCCCACGCCGCAGACAGGCCCCGAAGGAGGATG
CTGAGAGGGGATGGGAGAGGAGACAGAGAGGGCGAGCCTTGGATAGAGAA
GCTGGAAGAGCCAAGGTCTGGTACTGGCCACAGGAAAGAATCCTGGGTCA
CCC~TCAGATGCCAGCAAAATTGAGACAGCGGAGAACGGTTAGGTTCAAG
AGGAGTGGATGAAGACCCAGGAGCAGGAAGTGCAGGCTGAGATGGGACAA
GCAGAGGGTCAGCAGAGGCTGGGCTCAGAGAAAGGCAGAGACGTGTGGAA
ATACAGGCATGTCAGACCGTGCGATGGGCAGAAATATGGCGCCAGGGAGA
ACGGGAGCCCAGGTCCAGCTTTGAGACCGGGAACCGGGCAGAGGGGAAGG
GAGACAGACACAGAGAAGGACAGACATACAGGGAGCCAGGCAAATGCAGG
GCTTCTCTCCTCGGCCCCTTACCTGCGGCAGGAGTGACCAACCGGCACGC
TCACCCTCCAAGACTCCTGGCAGAGTAAGGAGCTGCTTCGGGAGGACAGA
GAGTAGGGATGGATGTGAGAGGGAGACTAGGATAGGGAGAGGATGGCAAA
CCAGACCAGACGGGTGGGGCAGAACCCTGGAACCGTGTTAAGCCCTCCCC
TCTTCCCCCTTCCATAGGAGACAGTGGGAACCGCCTGCCTACCCCTCACC
ACCCCTCGACTCCATCTATACCCAGTCTGGCTTGCTCAGAACATAAGGTT
CCCTGAGGACAAAGCCTAGCCTTTGTCACCTGGTTCTGACCCAGTCTGAC
CTGATGTTCCCAGCCCCTTATCACGTCCCCAGGGCAATGGGAACTAGGCA
GTGACGCACTGGGCCGCAGACTAAACCCCCAGCTTGCGTACTAGGTCCTC
AAGTGACCTGGAGATGGGGACAAGTAGCTTTCATCCCAGGGGGAAATGAG
TTGGCATATGTGCCTGCAGGAGATGGGAATGTGGGTTGACTACGGTCCCC
CCAAGGACATGGGTATAGGGTACAAGTCCCCTGGAGACAGATGTGTAATC
CTGAGTCCCACAGTGGGGCAGTGGAGGGCCCTAGGGAGTTGGAGACCATG
CAGGAGAGACCACATAATTGGTGGAAAGCAGAGAAGCCGACCCCCATCCG
TCCTACCCACCTCCACACTCTAGAGCTATATTGAGAGGTGACAGGAGATG
GTTTGGGAGGGGGAGCCTGGGAGCATGTTCCTGGGTGTGAGGGTGTAGGG
AAAGCCAGGGCAGCAGAGTCTGGCTTTGTTTCCTGAACACAATGTCCACT
TAGTCATAACAGGCATGGCTACTGCCTCTGAGAGGTGGCATCACTGGAGG
CAGGGAGGGGGCCACAAGGGCCTGAGGCGCTTGGGGACACTCTCCAAGA
AGGACATGTGAGTATGAGCCCATGAGGGTTGAGAGGCGACACCAGGGTT
CTACCTGGGGAGACGGGAGCGGACTGCAGAGCCCCACCCTGTGGAATGC
CAAGCTTGGGGCCCAGCTGGTGTAAATCCCGGGGATTGCCAGGGCCCCAG
TCAGCCTCAGCAGCACCTGCACCCTCTGGCAGCCCAGGGAGGCGGAAGGG
AGCACCCCCACCCTCACCCCTCCTGCCTCAGGCCCCGGGGATTAACGCCT
CTCCCACCCCCATCCCATCCCACAATGGGAGCAGAGGATGGCAGTGAAGG
GTAAAAGCTTCTGTGTGCAAATGTGCGTTTGGGTGTGCAAAACAACGCAG
AGGAAAATCTGCAAACTGAAGTATGTAAGAGTGGAAAACCCTCATGTGTG
```

-continued

```
TGTTAAGACTGGGCATGGACCCGTGGTGGCCAAGTCTGGACAGTAGATGG

CTGGACTGCGGGTCTGTGTGCACCTCTGCCATGGTGGCATGGGGGAACTC

CGTCTTCTGCTTGACAGGTCAGACAGTGGCCACTGTATCAGGAGCGTCGG

GGAGGGGCTGGGGGCTCCGGATGTGTCCCTAATGTAATGCAACCTCACGT

TCCCAGGAGGACACCTGCCTGCAGACAGGGGAAAACACAGAAAGAGAGGG

CAGCACGAAATTCTTTTCCTGACAAAGGGAAACTGAGTCAAGGACCCGGG

TAGTGGCGCCCCTCCCTGGGCGTCCTGGCTCCAGCAGCCAGGCCCCAGCA

CCATAGGGCTCCAGGACCAGAGAGGGTGGGGAGCTGCTCCCAGCCTGGGG

CCGTGTGAGGACAGGCCAGGGAGGAAAGGAGGAGGGGAGCCCGTGGCTGG

GAGGCAGGGGACAAGCCTCT

GGTCTGCAGGAGAAGGTGGCCCTCACCCCGTGTGCTCAACTCACCCTTCA

GATTAAAAATAACCAAGGTAAGGGCTTGATGGGGGGTGGCAGGGGGAG

GTGGTATGAGAAGTCCTGTCTTGCCACTATCGGCCCATCAGTCTTTTGGA

GGGGAGGAATGTGCCCAAGGACTAAAAAAAGGCCCTGGAGCCAGAGGGGC

TGGGGCGACAGACCTTTCATGGGCAAATCTGGAGTCCCGGTGTCCTCTTG

TCACCTCCAGAGCCAAGGGATCAAGGGAGGAGGGCTGGGAGGAGAGAGA

GGTGGAAGGGAGGGTCCCTCCGGAAGGACTCCAAATTTAGGCAGGGGGTG

GGGGCAGCGAAATATAAAGGAGTGTGCTCCAAGGACAGACTGACACTCCT

CTGAGCCAGGTAAGGTGGGGCTCAGGGTGGGAGCCCCCATCTCGAAAGGG

AATGGGGTGAGATCAGTCGGAGGCCCCAAGGGTTTCTGCTTGAACTGTCT

TGCTCCAGCCCTGGGAAGTTGCCCCCGACAGAGGGGGAGGTTCCCAGGGG

AAAACCAGAAACCTCTTTTCTTCTCCTACCGGCATGTCCTCCCCGGCTTT

CGTCTCTTCCATGTGCTTTCTTCCCCTTTGTCCCTCCTTGGATGGCTTCC

CTCTTGCAATCCAG~TTTTTTTTTTTTTTTTTTAAGGGAGGATAGTTA

TAATATTGTGATGGTTCTTGCCATACATCAACATGAATTGGCCACGGGTG

GTTCAGTTTTATTTTTCCTCTTGGTTTTTGTCAGCACTTGTCACTATCAT

ACTTCCTGGTCTGTCTCTCTTCCTGCCCCTCTTGGCTGTGTGCTCTAATC

TCCTTGCATCTCTCTGTTTCAAACGCAGATTCCACACCCTACTCCTTGCA

CTTTGACTAACTCTGCATCCTCTCTTCCCTGTCTCTCCGCCTCTCACCCG

CCCCTGACTGCCCCTTTCAGTCTGTCCCGCTCAGGTGACTCCCTGGCTTG

AGACTCACAGCTTGCTTCTCCCCGTGGGCTGCCCCCTTGTTCTTCATTCT

CCTTGTCTCTTCTCTCTGCTCAGCTGCACCTCTGTGGCTCACGGTCCAGG

GTCTTCAGGATTCTCTGTGAAGAGGTCAC
```

Example 2: TALEN-Mediated Targeted Insertion of Transforming Growth Factor-131 (TGF-β1) Gene into the Goat AAVS1 Locus AAVS1 locus, an integration site of adeno-associated virus 2, is used in the art as a nonpathogenic "safe harbor" for site-specific integration to achieve persistent and strong transgene expression [3]. Through TALEN-mediated gene targeting strategy, the hTGF-β1 gene was successfully integrated into the goat AAVS1 locus. As disclosed herein TALEN-AAVS1 can efficiently induce a double-strand break with cleavage efficiency of 2% in transfected goat fibroblast cells. The α-MHC-TGF-β1 expression cassette (8.5 kb) was knocked into the goat AAVS1 locus by co-transfecting goat fibroblast cells with TALEN-AAVS1 and α-MHC-TGF-β1 donor vector. Single cell fibroblast colonies were isolated from the transfected cells using puromycin-mediated positive selection. Among the 8 puromycin resistant clones, 6 (75%) were confirmed as correctly targeted by PCR and sequence analysis. These cell clones are used for transgenic goat production by SCNT. In addition, the target site sequence of goat TALEN-AAVS1 has 100% homology to that in the sheep and therefore can also be used for developing transgenic sheep by TALENs-mediated safe harbor (AAVS1) targeting.

Example 3: Production of Transgenic Cloned Goats

Figure 2:
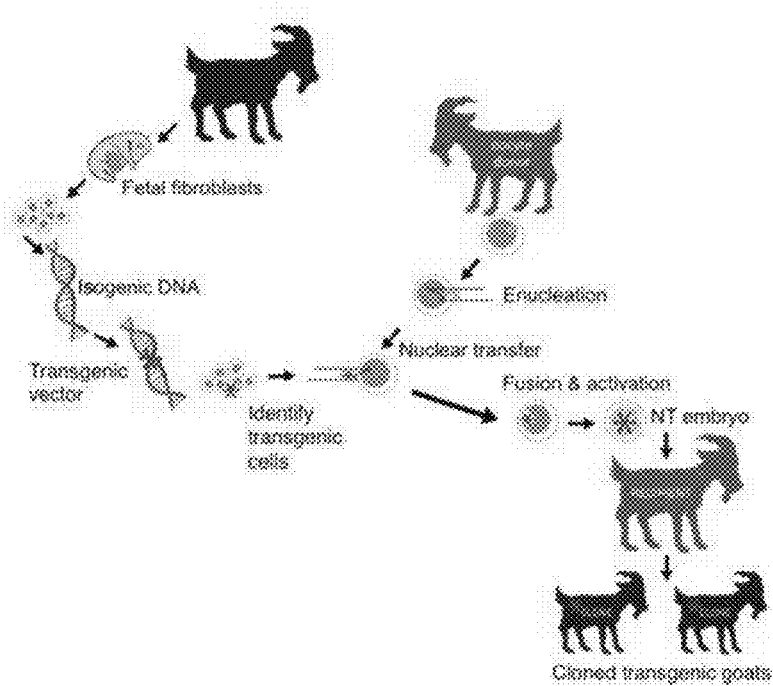
FIG. 2 depicts an outline of an embodiment of the Somatic Cell Nuclear Transfer (SCNT) procedure for TFG-β1 transgenic goat model development according to the present invention.

Somatic donor cells were adult, neonatal or fetal fibroblasts. Adult fibroblasts were obtained from a transgenic doe skin biopsy and neonatal fibroblasts from 1-5 day old transgenic kid skin biopsies. Fetal fibroblasts were isolated from 25-35 day-old fetus, then electroporated with a pcDNA3.1DV5-MHC-TGF-β1cys33ser vector, followed by G-418 selection, screening and subsequent use for SCNT. SCNT procedure is illustrated in FIG. 2. Oocytes with >4 layers of cumulus cells were collected by slicing abattoir ovaries and matured in vitro for 20-24 h. After being denuded, oocytes presenting a 1st polar body were enucleated and received a donor cell. Fused embryos were then activated for 5 min in 5 μM ionomycin followed by 4 h in 2 mM DMAP with 5 μg/ml cyclo-heximide. Activated embryos were cultured in G1.2 medium with 5 mg/ml BSA for either 12 or 60 hours post activation, followed by surgical transfer into the oviducts of recipients synchronized to show estrus within 12 hours of SCNT. Overall 376 embryos were transferred to 23 recipients. The results are summarized in the Table 1. No pregnancy losses were observed after Day 30 of gestation.

As depicted in FIG. 2 a matured oocyte was enucleated and a transgenic donor cell was transferred under the zona pellucida of the enucleated oocyte. The somatic cell and the oocyte were then fused. After short in vitro culture one-cell embryos were transferred into a recipient and transgenic cloned goats were born after completion of gestation.

TABLE 1

| Cell Line | Hours in Culture | # Embryos Transferred | # Recipients | Pregnant @ Day 30 (%) | # Live Offspring (%) |
|---|---|---|---|---|---|
| Adult Fibroblast | 12 | 45 | 3 | 1 (33.3) | 2 (4.4) |
|  | 60 | 85 | 6 | 0 (0) | 0 (0) |
| Fetal Fibroblast | 12 | 156 | 9 | 4 (44.4) | 6 (3.8) |
|  | 60 | 90 | 5 | 1 (20) | 1 (1.1) |
| Total | 12 | 201 | 12 | 5 (41.7) | 8 (3.98)[a] |
|  | 60 | 175 | 11 | 1 (9.1) | 1 (0.57)[b] |

[a,b]Values in the same column with different superscripts are significantly different (P = 0.0143) as determined by a χς test with a two-tailed P-value. An effect of cell line on number of live offspring was not apparent (P = 0.289).

Figure 3:
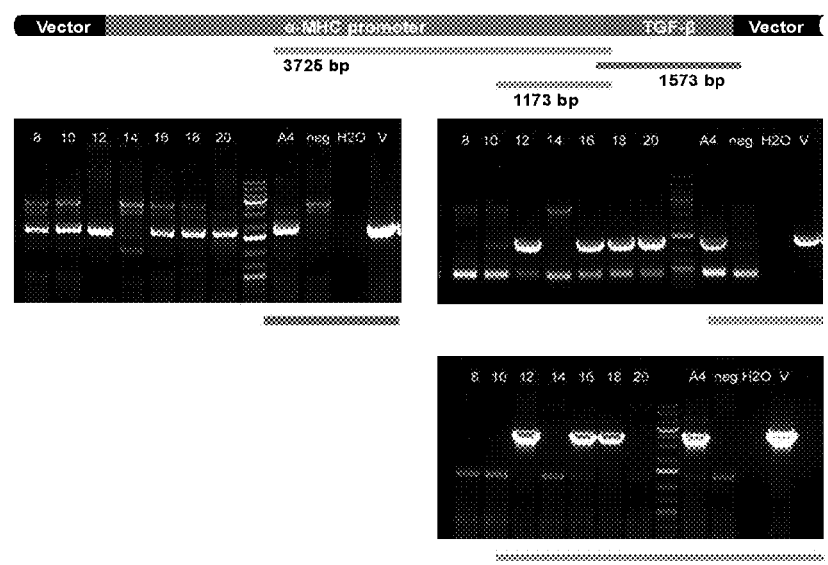
FIG. 3 depicts PCR analysis of cloned offspring according to the present invention.

All kids were born live (42% of recipients receiving embryos cultured for 12 hours gave birth, compared to only 9% when cultured for 60 hours). Production of transgenic goat via SCNT was successful. PCR results confirmed that 3 out of 7 clones are positive for both α-MHC and TGF-β1 (FIG. 3). As depicted in FIG. 3 Lanes 8, 10, 12, 14, 16, 18 and 20 are cloned goats; lane A4 is a positive control (cells); lane neg is wild type goat genomic DNA; lane H2O is water only (non-template control); and lane V is a vector.

Additionally, we produced transgenic cloned goat using neonatal fibroblasts derived from skin biopsy (re-cloning process). Development to term rate was 5/23 (21.7%).

Example 4: Cardiac Specific Overexpression of TGF-β1 Increases Susceptibility to Atrial Fibrillation in Transgenic Goats Under intracardiac echocardiogram visualization and fluoroscopic guidance cardiac biopsies were obtained from the ventricular septum. Skeletal muscle biopsies were also collected from each of the animals. Analysis of gene expression revealed that goats #12 and #16 had cardiac specific hTGF-β1 expression and that goat #18 had no detectable hTGF-β1 mRNA. None of the transgenic goats expressed hTGF-β1 in the skeletal muscle. Different levels of cardiac gene expression are not surprising as random integration was used for the production of these 3 transgenic founder animals. Additionally, a 2 to 3.5-fold increase in cardiac expression of collagen 1 and 3 was observed in goat #12 compared to goat #18. AF inducibility testing was performed on seven animals (Goats #12, #16 and #18, and 4 control animals) using rapid pacing at 50 Hz for 30 sec at three different locations in the right atrium. Sustained AF was defined as an episode of AF lasting more then 30 seconds. Three out of four AF inducibility tests resulted in sustained AF episodes in goat #12. The first AF episode converted to sinus rhythm after 3 min 15 sec. The other two lasted 12 and 16 minutes requiring cardioversion. None of the control animals developed AF following the AF induction test.

The increase in cardiac collagen level in the hTFG-β1 transgenic model is indicative of fibrosis initiation. The data suggest that there is a relationship between the level of hTGF-β1 expression and susceptibility to AF induction in this goat model. This model of hTGF-β1 overexpression represents a dramatic step forward in the development of large animal models with a substrate for atrial fibrillation.

Example 5: Production of TGF-β1 Transgenic Goat by TALENs-Mediated Safe Harbor (AAVS1) Targeting Goat AAVS1 gene was amplified by PCR and sequenced. AAVS1 gene was subjected to TALENs target analysis. The Goat AAVS1 gene sequence is as follows (SEQ ID NO. 2):

```
GCCCCGCCCCCTCCCAGGTTCGCAGGGGCCTGGCAATCCCGCATGGCCT
TGGGCCCCAGGGTCCGGCTGTCTCCCTACCAGGGACACGGCAGGGCGGTG
GTCAGCTCTCCTGGAGAGTCTGCTGGGTCTGAGGAGGAGGGCCTGGGTCT
CTTCCCTTGGGTTCAGCTCTGGGGGCCCATCCTCCATGGTGACTGGGGTG
CGTCTCCTGAACAAGCATAGTTCGGGATCCCTACAGCTCCTCTCCTCTCT
GGCCAGCTTCTCCTCTCACGGTCCCCAGTGAGCCCCAGAGGCCTGCCTGG
CGTGGCCACCGGGAAGCCAGGCTGTGCAGGGCTGGGGGTGCCCTGCGGAC
ATGGTGCCTTCCAGGGACCTTGGGGTCTTCCTCTGGAGCCTTGCTCGGTC
GGCCCTGGGTCCCCCTCGAGGCCCTGCCTTGCAAGGCACGTGGAGGGGTC
CGGGGTGGTGAGGGTGACCCCCCGCCGTGCCCCCCAGGCCTGCATTGACG
AGAACCTTGAGGTGGTGCGCT
```

Figure 4:
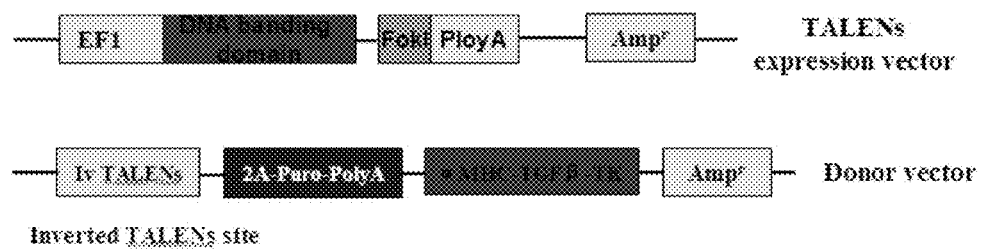
FIG. 4 is a block diagram depicting an embodiment of a Transcription TALENs expression vector and donor vector according to the present invention.

TALENs expression vector and donor vector were constructed (FIG. 4). The target sequence of TALEN targeting goat AAVS gene (SEQ ID NO. 3) is as follows:

```
TCCGGCTGTCTCCCTACCAGGGACACGGCAGGGCGGTGGTCAGCTCTCCT
GGA.
```

Figure 5:
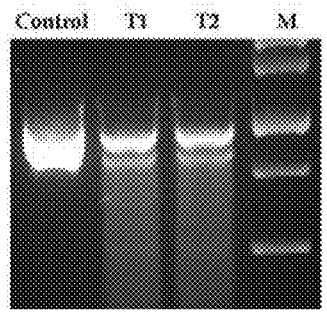
FIG. 5 depicts the results of a TALENs activity test assay according to the present invention.
Figure 6:
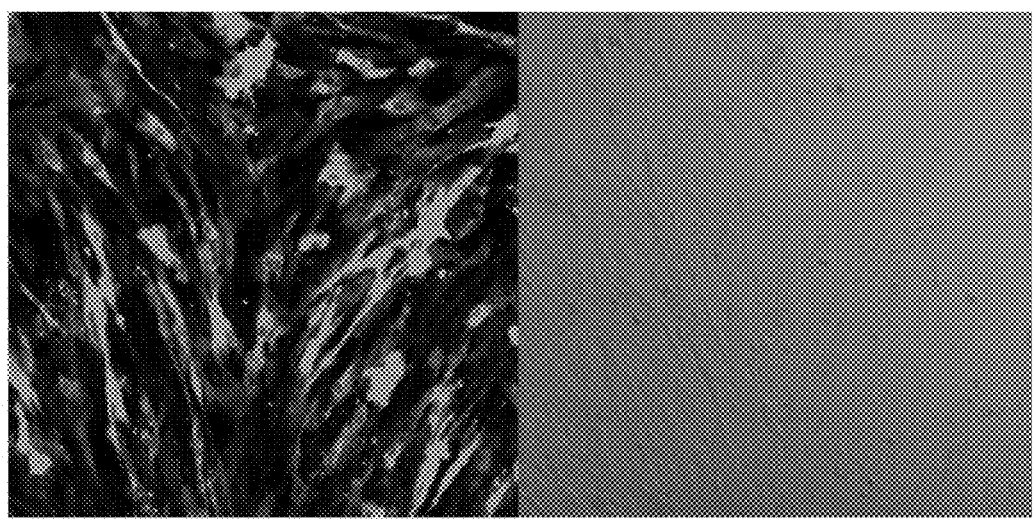
FIG. 6 depicts GFF 72 hours after transfection according to the present invention.
Figure 7:
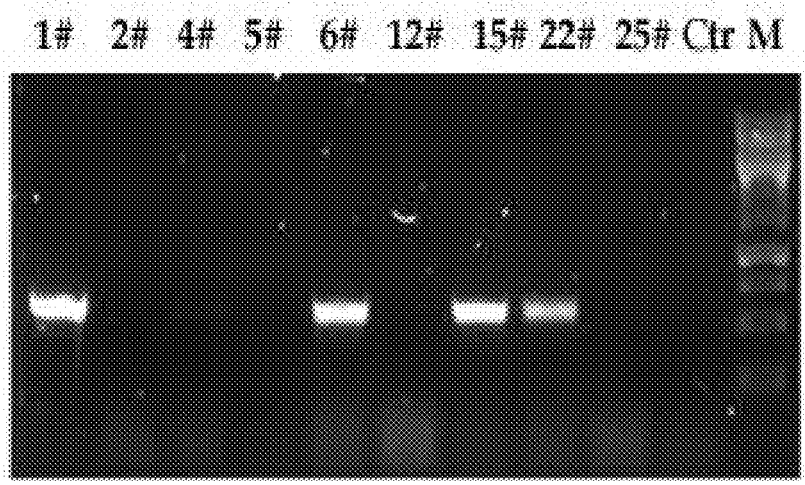
FIG. 7 depicts the PCR and sequence analysis of 5' junction of transgene/AAVS1 of cell clones according to the present invention. TALEN binding sites are highlighted. Missing sections indicate 2-6 nucleotide random deletions in the TALEN targeted cut site.
Figure 8:
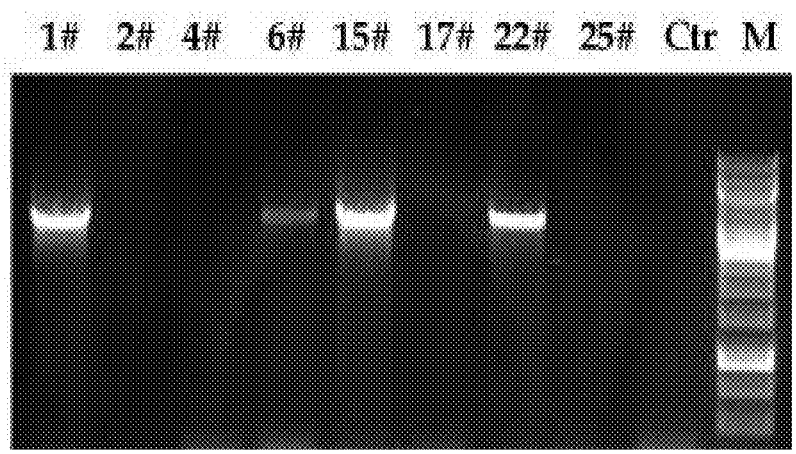
FIG. 8 depicts the PCR and sequence analysis of 3' junction of transgene/AAVS1 of cell clones according to the present invention. TALEN binding sites are highlighted. Missing sections indicate 2-6 nucleotide random deletions in the TALEN targeted cut site.

A TALENs activity test assay revealed a TALENs targeting efficiency of 2% (FIG. 5). Transgenic goat fibroblasts were generated by TALENs-mediated safe harbor (AAVS1) targeting (FIG. 6). Cells were then subjected to puromycin selection. The 3' and 5' junctions of transgene/AAVS1 were tested by PCR (FIG. 7 and FIG. 8). FIG. 7 illustrates PCR and sequence analysis of 5' junction of transgene/AAVS1 of cell clones. The TALEN binding sites in FIG. 7 are the first 10 nucleotides and last 9 nucleotides of each of SEQ ID NOs: 35-39. Missing sequence indicates the presence of 2-6 nucleotide deletions in the TALEN targeted cut site.

FIG. 8 illustrates PCR and sequence analysis of 3' junction of transgene/AAVS1 of cell clones. The TALEN binding sites in FIG. 8 are the first 10 nucleotides and last 10 nucleotides of each of SEQ ID NOs: 40-44. Missing sequence indicates the presence of 2-6 nucleotide deletions in the TALEN targeted cut site.

Example 6: Homologous Recombination Method

Homologous recombination method was used for production of a transgenic goat model that overexpresses TGF-β1 in the myocardium, employing the following steps: (a) characterizing the caprine cardiac α-myosin heavy chain (α-MHC) genomic locus; (b) designing and building a gene targeting vector for site specific insertion of a constitutively active human TGF-β1 into the α-MHC locus; (c) generating TGF-β1 transgenic clonal fibroblast populations; and (d) producing cloned TGF-β1 transgenic goats via SCNT.

Cardiac α-Myosin Heavy Chain Locus Characterization

Figure 9:
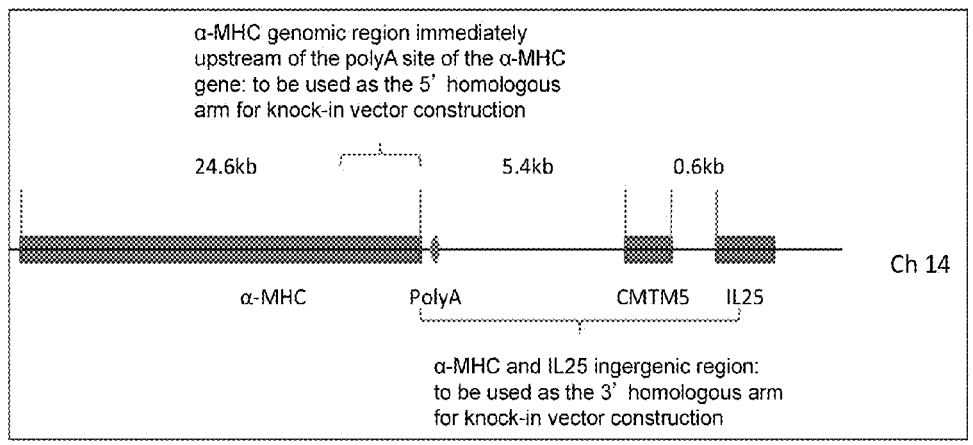
FIG. 9 depicts the genomic configuration of the alpha-Myosin Heavy Chain (α-MHC) locus in mouse (NCBI Reference Sequence: NT_039606.7) according to the present invention, (Genes are not shown to scale)

The goat α-MHC locus must be fully characterized to allow knock-in of the human TGF-β1. Comprehensive NCBI database searches indicated that the sequence of the goat α-MHC locus was not available. However, sequence analysis of the α-MHC locus in 12 diverse mammalian species (*Mus musculus, Rattus norvegicus, Bos taurus, Canis lupus, Homo sapiens, Macaca mulatta, Oryctolagus cuniculus, Callithrix jacchus, Nomascus leucogenys, Cricetulus griseus, Pan troglodytes,* and *Pongo abelii*) revealed that not only the α-MHC coding sequences but also its genomic configuration with neighboring genes are highly conserved. FIG. 9 depicts the genomic configuration of the mouse α-MHC locus on mouse chromosome 14 and the neighboring CKL-lie MARVEL trans-membrane member 5 (CMTM5) and interleukin 25 (IL25) genes. The sequence of the goat α-MHC locus was isolated using conserved sequences in the α-MHC locus. Homologous sequences in the α-MHC and IL25 genes were used to design PCR primers that amplify 6 kb to 30 kb (depending on where the 5' PCR primer is placed in the α-MHC region) of goat genomic DNA. The amplified segment was sufficient for designing and constructing the knock-in vector.

b) Design and Construction of the Knock-in Vector

To achieve a highly cardiac-specific expression of TGF-β1, an internal ribosome entry site (IRES) TGF-1 construct (IRES-TGF-β1) was knocked in immediately upstream of the polyadenylation site of the goat α-MHC gene through homologous recombination. Such a strategy allows tight expression control of a transgene by the endogenous goat α-MHC regulatory sequences. The goat α-MHC locus was fully characterized for the knock-in vector construction and conserved sequences in the α-MHC and IL25 genes were used to design PCR primers that amplify goat genomic DNA (FIG. 11).

Figure 10:
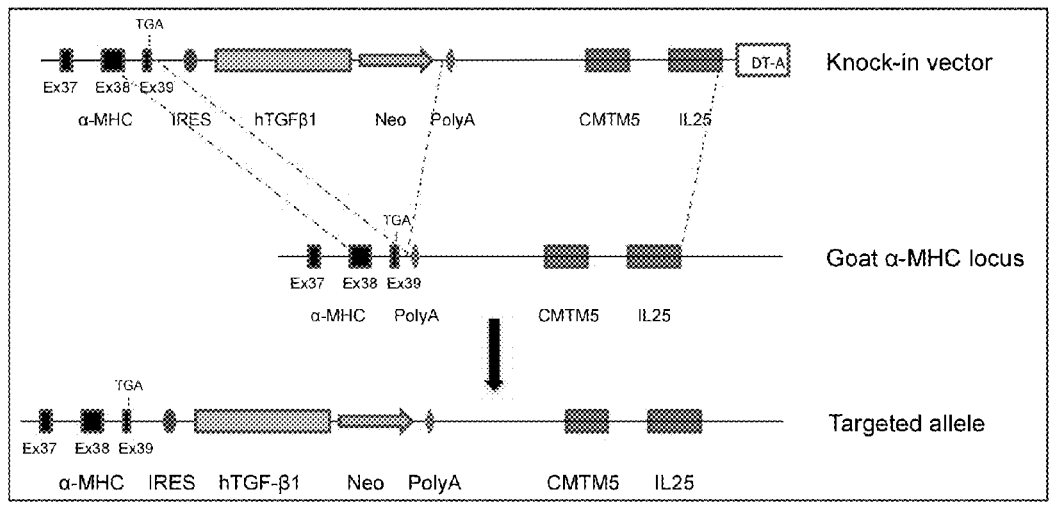
FIG. 10 depicts an embodiment of a knock-in scheme for a goat α-MHC vector according to the present invention.

As depicted in FIG. 10 the Internal Ribosome Entry Site (IRES)-hTGF-β1 construct is knocked into the goat α-MHC locus. Square and narrow boxes represent the last 3 exons of α-MHC, diamond represents the goat α-MHC polyA signal sequence, oval represents the IRES sequence, long box represents the hTGF-β1 coding sequence, arrow represents the Neo expression cassette, rectangular boxes represents the CMTM5 and IL25 gene loci, and larger rectangular box represents the DT-A expression cassette. The stop codon (TGA) of α-MHC located in exon 39 is also indicated.

Figure 11:
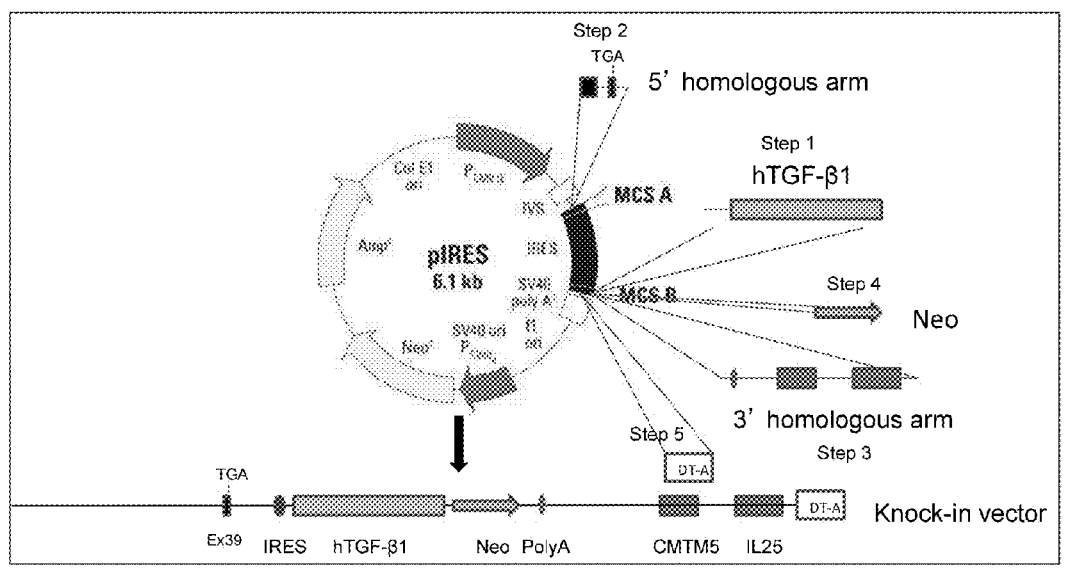
FIG. 11 depicts an embodiment of the steps in knock-in vector construction according to the present invention.

The vector construction was achieved in two phases following the steps as depicted in FIG. 11. The first phase was to clone and fully characterize: an ~9 kb goat genomic fragment covering the polyadenylation site of the goat α-MHC gene. This sequence includes ~7 kb of the goat intergenic region between the α-MHC and IL25 genes and ~2 kb of goat genomic DNA immediately upstream of the goat α-MHC polyA site. This sequence was cloned as two separate fragments into pBluescriptII SK(−) (Stratagene) and is fully characterized by sequencing. These two goat genomic fragments are used as the 3' (~7 kb fragment) and 5' (~2 kb fragment) homologous arms of the knock-in vector construct.

The second phase involved the following steps:
An IRES-hTGF-β1 construct was built by subcloning the coding sequence of TGF-β1 (provided by Dr. Loren J. Field, Riley Heart Research Center, Indiana University) into the MCS B locus of vector pIRES (Clontech; Cat#631605) (step 1, FIG. 12).

Using the appropriate restriction sites, the 5' and 3' homologous arms were subcloned into the MCS A and MCS B sites of the above generated pIRES-hTGF-β1 vector (steps 2 and 3, FIG. 11).

The Neo expression construct (positive selection) and the DT-A construct (negative selection) were inserted into the vector as depicted in FIG. 11 (steps 4 and 5). The order of the steps may be modified according to the sequences of the goat genomic DNA fragments to be used for the vector construction and depending on the available restriction enzymes. The knock-in vector was characterized by restriction mapping followed by DNA sequencing.

c) Transfections of Goat Fetal Fibroblasts

Passage 1-2 primary goat fetal fibroblasts (GFFs) were used for transfections. GFFs were cultured in DMEM (Hy-Clone Laboratories) containing 2 mM L-glutamine, 1 mM sodium pyruvate and supplemented with 15% of FBS (Hy-Clone Laboratories) at 38.5 degrees C. in a humidified atmosphere of 5% CO2 in air for 4-6 days. Upon reaching 70-80% confluency, cells were harvested. The knock-in vector was linearized for transfection. The Neon™ Transfection System that employs a pipette tip as an electroporation chamber was used for electroporation. This method has been efficiently used for transient and stable transfection of GFFs. About $1.0 \times 10^7$ exponentially growing GFF cells were disaggregated and washed in PBS twice, then mixed with a buffer containing 10 μg linearized DNA. Two million cells were loaded per 100 μl electroporation tip then placed in the pipette station and subjected to a single 1.5 kV pulse with the width set at 20. Forty-eight hours after transfection, the cells were selected using 400 μg/ml of G418 for 2 weeks or until colonies are formed. The Neo-resistant colonies were harvested and transferred to two replica plates, one for genomic DNA extraction (24-well plates) and the other for animal cloning (48-well plates).

d) Genotyping Transfected Cells.

Genomic DNA was isolated using a Puregene DNA extraction kit (GentraSystem). To identify each homologous recombination event that occurred at the goat α-MHC locus, diagnostic genomic PCRs were performed with appropriate positive and negative controls. The PCR products are sequenced to confirm the knock-in.

Example 7: Expression of TGF-β1 in Transgenic Goats

Frozen tissue biopsies were homogenized using QIAshredder columns (Qiagen, Valencia, Calif.). RNA was isolated using RNeasy Plus Micro Kit (Qiagen, Valencia, Calif.) according to manufacturer's instructions. Total RNA was reverse transcribed using the SuperScript VILO cDNA synthesis kit (Life Technologies) according to the manufacturer's protocol. Because of the small amount of starting material, the RNA was preamplified in a reaction containing 50 nM each primer using the TaqMan PreAmp Master Mix (Life Technologies). TGF-β primers used were (SEQ ID NO. 4) GAGTTGTGCGGCAGTGGTTGA and (SEQ ID NO. 5) GTAGTGAACCCGTTGATGTCCA.

The thermocyling parameters used were 1 cycle of 95° C. for 10 minutes followed by 14 cycles of 95° C. for 15 seconds and 60° C. for 4 minutes. After preamplification, quantitiative PCR was carried out using the same primers and GoTaq qPCR Master Mix (Promega). Thermocycling parameters used were 1 cycle of 95° C. for 2 minutes followed by 40 cycles of 95° C. for 15 seconds and 62° C. for 1 minute, followed by a melt curve cycle.

Example 8: PCR Screening

Kids were screened for the presence of the transgene by PCR using blood genomic DNA. PCR primers used were:

```
                                     (SEQ ID NO. 6)
αMHC-0_F:       TCTCTTGTGCTACCCAGCTCTA (SEQ ID NO. 7)
αMHC-2.4K_R:    GAGGTCACTTGAGGCTCCTGT (SEQ ID NO. 8)
αMHC-1.9K_F:    GTATGAGCACCAGAACAGCAGA (SEQ ID NO. 9)
aMHC-4.4K_F:    GAAGTTCTCAGTGGCAGGAGGTT (SEQ ID NO. 10)
αMHC-5.2K_F:    CCACACCAGAAATGACAGACAGA (SEQ ID NO. 11)
TGF-200_R:      GATGCGCTTCCGCTTCACCA (SEQ ID NO. 12)
pcDNA3.1_R:     AGTGGCACCTTCCAGGGTCAA (SEQ ID NO. 13)
neo_F:          AGACAGGATGAGGATCGTTTCGCA (SEQ ID NO. 14)
neo-R:          GCGGTGGAATCGAAATCTCGTGAT
```

PCRs were carried out in a reaction using Herculase II polymerase (Agilent), 100 ng of genomic DNA, and primers at a concentration of 500 nM, 1× buffer, and 250 μM dNTPs. Thermocycling parameters were 1 cycle of 95° C. for 2 minutes followed by 35 cycles of 95° C. for 20 seconds, 61° C. for 20 seconds, and 72° C. for a variable time depending on the length of the amplicon, and a final extension of 72° C. for 8 minutes.

Example 9: Vector Construction—G α-MHC-hTGF-β1-TK

The goat promoter was first cloned using primers BaMHC-4K_F1 and BaMHC_ex2_R1, which were designed based on the bovine genomic sequence in this region. These primers were used to amplify the promoter by PCR from goat genomic DNA, and the resulting PCR product was cloned into pCR4Blunt-TOPO.

Figure 12:
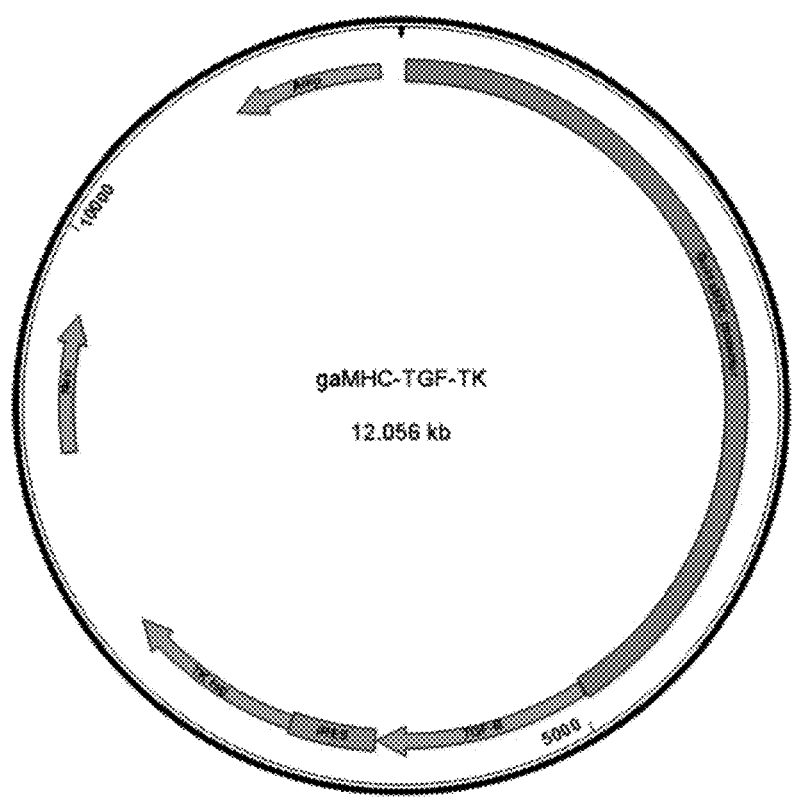
FIG. 12 depicts an embodiment of the assembled gaMHC-TGF-TK vector according to the present invention.

To create the G-αMHC-TGF-β1-TK construct, the constituent parts were amplified individually. The goat αMHC promoter was amplified from the construct described above using primers IF-GaMHC-5_F2 and IF-GaMHC-T3_R. The TGF-β portion was amplified from pcDNA3.1ID-αMHCpro-TGFcys33ser using primers IF-M3-TGF5_F and IF-TGF3-TK5_R. The TK tag was cloned from pLOX-gfp-iresTK using primers IF-T3-TK_5 F and IF-TK3 R2. The vector backbone was generated by amplifying pcDNA3.1D-aMHCpro-TGFcys33ser with primers IF-TK3-V F and IF-V-GaMHC-5 R. These four pieces of DNA were then mixed in a reaction with the In-Fusion HD (Clontech) reagent. This enzyme combined the four pieces of DNA at the points where the sequences overlapped to created one circular molecule of DNA, the G α-MHC-hTGF-β1-TK construct (FIG. 12).

TABLE 2

Primer sequence for gene expression analysis and vector construction

PRIMER SEQUENCE

GENE EXPRESSION ANALYSIS

| | |
|---|---|
| COL1A1-F | TGGTGCTGACGGACCTGCT |
| COL1A1-R | CACACCACGCTGTCCAGCAA |
| COL1A2-F | CTGGTGAGCCTGGTGAACCT |
| COL1A2-R | CATCCTCACCAGCCTTGCCA |
| COL3A1-F | CACGCAAGGCCGTCAGACTA |
| COL3A1-R | AGGGCCAATGTCCGCACCA |
| FN1-F | CACACCCTTGACTCCTGTTGT |
| FN1-R | CTCTTCACTCAGCTCATACTCCA |
| TGFB-F | GAGTTGTGCGGCAGTGGTTGA |
| TGFB-R | GTAGTGAACCCGTTGATGTCCA |
| IF-V-GaMHC-5_R | CAGCAGATCTTCGACGTCAGGTGGCACTT |
| IF-GaMHC-5_F2 | GTCGAAGATCTGCTGCCCCTTTGGAAGAAGCAGA |
| IF-GaMHC-T3_R | GGTGGCTCGAGGTGACCTCTTCACAGAGAATCCTGA |

TABLE 2-continued

Primer sequence for gene expression analysis and vector construction

PRIMER SEQUENCE

VECTOR CONSTRUCTION

| | |
|---|---|
| IF-M3-TGF5_F | TCACCTCGAGCCACCACACCAGCCCTGTT |
| IF-TGF3-TK5_R | TGGGAATTCGCGGGACCTCAGCTGCACTT |
| IF-T3-TK5_F | TCCCGCGAATTCCCACCATATTGCCGTCTT |
| IF-TK3_R2 | GACCGATCGATCCAAAGCCCAGGCAAACACGTT |
| IF-TK3-V_F | TTGGATCGATCGGTCATCATCACCATCACCAT |
| BaMHC-RK_F1 | GCTGCCCCTTTGGAAGAAGCAGA |
| BaMHC_Ex2_R1 | GTGACCTCTTCACAGAGAATCCTGA |

TABLE 2

Primer sequence for gene expression analysis and vector construction

GENE EXPRESSION ANALYSIS PRIMER SEQUENCE

| | | |
|---|---|---|
| COL1A1-F | (SEQ ID NO. 15) | TGGTGCTGACGGACCTGCT |
| COL1A1-R | (SEQ ID NO. 16) | CACACCACGCTGTCCAGCAA |
| COL1A2-F | (SEQ ID NO. 17) | CTGGTGAGCCTGGTGAACCT |
| COL1A2-R | (SEQ ID NO. 18) | CATCCTCACCAGCCTTGCCA |
| COL3A1-F | (SEQ ID NO. 19) | CACGCAAGGCCGTCAGACTA |
| COL3A1-R | (SEQ ID NO. 20) | AGGGCCAATGTCCGCACCA |
| FN1-F | (SEQ ID NO. 21) | CACACCCTTGACTCCTGTTGT |
| FN1-R | (SEQ ID NO. 22) | CTCTTCACTCAGCTCATACTCCA |
| TGFB-F | (SEQ ID NO. 23) | GAGTTGTGCGGCAGTGGTTGA |
| TGFB-R | (SEQ ID NO. 24) | GTAGTGAACCCGTTGATGTCCA |

VECTOR CONSTRUCTION

| | | |
|---|---|---|
| IF-V-GaMHC-5_R | (SEQ ID NO. 25) | CAGCAGATCTTCGACGTCAGGTGGCACTT |
| IF-GaMHC-5_F2 | (SEQ ID NO. 26) | GTCGAAGATCTGCTGCCCCTTTGGAAGAAGCAGA |
| IF-GaMHC-T3_R | (SEQ ID NO. 27) | GGTGGCTCGAGGTGACCTCTTCACAGAGAATCCTGA |
| IF-M3-TGF5_F | (SEQ ID NO. 28) | TCACCTCGAGCCACCACACCAGCCCTGTT |
| IF-TGF3-TK5_R | (SEQ ID NO. 29) | TGGGAATTCGCGGGACCTCAGCTGCACTT |
| IF-T3-TK5_F | (SEQ ID NO. 30) | TCCCGCGAATTCCCACCATATTGCCGTCTT |
| IF-TK3_R2 | (SEQ ID NO. 31) | GACCGATCGATCCAAAGCCCAGGCAAACACGTT |
| IF-TK3-V_F | (SEQ ID NO. 32) | TTGGATCGATCGGTCATCATCACCATCACCAT |
| BaMHC-4K_F1 | (SEQ ID NO. 33) | GCTGCCCCTTTGGAAGAAGCAGA |
| BaMHC_ex2_R1 | (SEQ ID NO. 34) | GTGACCTCTTCACAGAGAATCCTGA |

Example 10: Phenotype Characterization of TGF-β(Beta)1 Transgenic Goats

Phenotype characterization was performed by: (a) Electro-cardiography (ECG); (b) Ventricular gene expression profiling; and (c) Confocal microscopy of the right ventricle biopsy samples.

a) ECG Evaluation

ECG data were collected on eleven animals (eight hTGF-B1 expressing and three controls) using PowerLab hardware and associated LabChart software (ADInstruments, Inc.). ECGs were collected monthly starting at six months of age. At least 50 full heart cycles were recorded for each animal. Since these transgenic goats (TGs) were derived from different hTGF-B1 transgene integration events and consequently exhibited different expression levels, we expect they will also have different phenotypic characteristics such as differing degrees of fibrotic changes. Our preliminary data show that in the highest expressing animal (TG12), the P-wave duration increased by more than 65% while QRS duration increased by only 17% compared to control animals. P-wave prolongation is commonly viewed as a marker of altered atrial conduction and an intermediate step to AF.

b) Gene Expression.

In total, cardiac biopsy samples were collected from the right ventricular (RV) septum of 8 transgenic and 6 control animals. Seven of these samples (four transgenic and 3 controls) were processed and the rest of the samples were collected recently and the analysis is underway. The results revealed that transgenic goats TG12, TG16, TG18 and TG20 expressed different levels of transgene-derived hTGF-β1 mRNA with TG12 expressing the highest level among the group (FIG. 13). Different levels of cardiac gene expression are not surprising as random integration was used to produce these transgenic animals. Since the biopsy samples were not large enough to assess TGF-β1 bioactivity, the effect of hTGF-β1 was evaluated indirectly by measuring collagen and fibronectin mRNA levels as well as fibroblast and extracellular matrix (ECM) volumes in the RV samples. In contrast to mice, where ventricular type 1 collagen mRNA expression was not elevated, we observed a 5-fold increase in both COL 1A1 and FN1 mRNA levels in the highest expressing animal (TG12) compared to controls with increased in ECM and fibroblast fraction (see confocal data below).

c) Fluorescent Labeling, Confocal Microscopy and Image Analyses.

TGF-β1 is known to induce cardiac fibroblast transdifferentiation into myofibroblasts, which are more mobile and contractile, and produce more ECM proteins. Therefore, we are assessing changes in fibroblast, ECM and myofibroblast contents using fluorescent labels for fibroblasts, myofibroblasts and the extracellular space. Using immune-labeling and 3D confocal microscopy (FIG. 14), we observed a 38.5% increase in the proportion of fibroblasts (from 2.6 to 3.6%) and a 17.0% increase in the ECM volume (from 21.2 to 24.8%) in an RV biopsy sample of a 12-months old TG compared to a control (FIG. 2). A RV biopsy sample from the same TG collected at 18 months showed a further increase in ECM volume by 12.9% (from 24.8% to 28%) without an additional increase in fibroblast ratio. These findings suggest progressive structural remodeling of cardiac tissue over time in these transgenic goats.

Example 11: Induction of Atrial Fibrillation in TGF-β1 Transgenic Goats Via Rapid Atrial Pacing (RAP)

AF inductions were conducted in the right atrium by two methods: burst pacing at 50 Hz for 30 sec and a single premature stimulus. Eight transgenic and three control goats at 12-14 months of age weighing between 27 and 36 kg (30.6±2.7 kg) were used for this study. AF was defined as an episode of rapid irregular atrial rhythm lasting more than 30 seconds after termination of rapid pacing. All 4/4 (100%) transgenic animals from the highest expressing TG12 genetic line were susceptible to AF induction generated by a single premature stimulus and ¾(%) exhibited arrhythmias after burst pacing. Three of 4 animals had AF episodes lasting at least 10 minutes and requiring cardioversion with a single 100 J shock. Only ¼ (25%) remaining transgenic animals (a group with a low TGF-β1 expression) was susceptible to AF induction. No arrhythmias were induced in the control animals regardless of the induction method. These data strongly indicate that there is a relationship between the level of hTGF-β1 expression and susceptibility to AF induction in this goat model.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

REFERENCES

1. Nakajima H, Nakajima H O, Salcher O, Dittie A S, Dembowsky K, et al. (2000) Atrial but not ventricular fibrosis in mice expressing a mutant transforming growth factor-beta(1) transgene in the heart. Circulation research 86: 571-579.
2. Verheule S, Sato T, Everett Tt, Engle S K, Otten D, et al. (2004) Increased vulnerability to atrial fibrillation in transgenic mice with selective atrial fibrosis caused by overexpression of TGF-beta1. Circulation research 94: 1458-1465.
3. Zou J, Sweeney C L, Chou B K, Choi U, Pan J, et al. (2011) Oxidase-deficient neutrophils from X-linked chronic granulomatous disease iPS cells: functional correction by zinc finger nuclease-mediated safe harbor targeting. Blood 117: 5561-5572.

What is claimed is:

1. A transgenic goat model for cardiac fibrosis comprising: a transgenic goat comprising in its genome a nucleic acid encoding a mutant human transforming growth factor β1 (hTGF-β1) protein operably linked to an α-myosin heavy chain (α-MHC) promoter, wherein the mutant hTGF-β1 protein comprises a cysteine to serine substitution at amino acid residue 33 of the wild-type hTGF-β1 protein which prevents covalent binding of the mutant hTGF-β1 protein to a latency-associated peptide (LAP) and a latent TGF-β1-binding protein 1 (LTBP-1), wherein the transgenic goat expresses the hTGF-β1 mutant protein in cardiac tissue and where the transgenic goat develops cardiac fibrosis.

2. The model of claim 1, wherein the goat exhibits at least one of atrial fibrosis, elevated levels of extracellular matrix (ECM) gene expression, increased ECM volume, elevated ventricular fibroblast fraction, or increased susceptibility to atrial fibrillation (AF) induction.

3. The model of claim 1, wherein the α-MHC promoter is a goat α-MHC promoter.

4. The model of claim 1, wherein the α-MHC promoter has a sequence according to SEQ ID NO. 1.

5. The model of claim 2, wherein the atrial fibrosis develops progressively.

* * * * *